United States Patent [19]

Tashiro

[11] Patent Number: 4,791,912
[45] Date of Patent: Dec. 20, 1988

[54] ENDOSCOPE

[75] Inventor: Yoshio Tashiro, Hachioji, Japan

[73] Assignee: Olympus Optical Co., Ltd., Japan

[21] Appl. No.: 127,563

[22] Filed: Dec. 2, 1987

Related U.S. Application Data

[63] Continuation-in-part of Ser. No. 923,039, Oct. 24, 1986, abandoned.

[30] Foreign Application Priority Data

Oct. 25, 1985 [JP] Japan ............................. 60-239014
Oct. 30, 1985 [JP] Japan ............................. 60-243374

[51] Int. Cl.⁴ ............................................... A61B 1/00
[52] U.S. Cl. ..................................................... 128/4
[58] Field of Search ............................ 128/3, 4, 5, 6, 7

[56] References Cited

U.S. PATENT DOCUMENTS

| | | |
|---|---|---|
| 3,261,351 | 7/1966 | Wallace ..................... 128/6 |
| 4,294,234 | 10/1981 | Matsuo ..................... 128/6 |
| 4,586,491 | 5/1986 | Carpenter ................. 128/6 |
| 4,674,496 | 6/1987 | Svadjian et al. ........... 128/4 X |
| 4,705,023 | 11/1987 | Arai ......................... 128/4 |
| 4,732,139 | 3/1988 | Kawashima et al. ...... 128/6 |

FOREIGN PATENT DOCUMENTS 60-210233 10/1985 Japan .
61-48701 4/1986 Japan .

Primary Examiner—William H. Grieb

[57] ABSTRACT

Disclosed is a construction of an endoscope with channels into which medical instruments are to be inserted, and more specifically, an arrangement of components constituting the channels in an operating section of the endoscope, and a mounting structure for fixing the channels in the operating section. The endoscope comprises an insertion section, the operating section, an insertion member having channel holes and disposed in the insertion section, a support tube disposed in the operating section and connected to the insertion member, the support tube having a notch, channel ducts, one end of each being connected to each corresponding channel hole of the insertion member, mouthpiece sockets each connected to the other end of the channel ducts corresponding thereto, channel mouthpieces, one end of each being removably connected to each corresponding mouthpiece socket, and the other end of each being formed with an opening, a cover member surrounding the periphery of the notch, and having opening portions into which the channel mouthpieces are to be inserted, and a support member fixed in the notch, and having retaining portions adapted to engage the mouthpiece sockets.

20 Claims, 8 Drawing Sheets

FIG. 5A
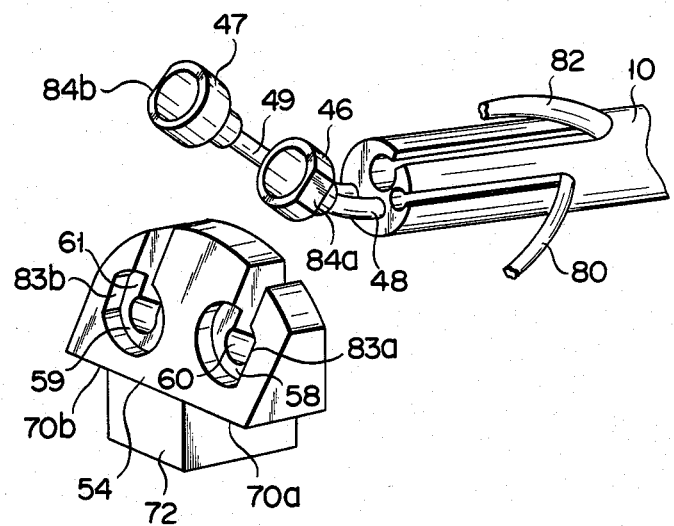
FIG. 5B  FIG. 5C  FIG. 5D
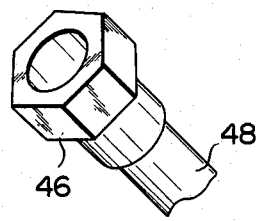 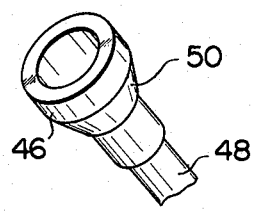 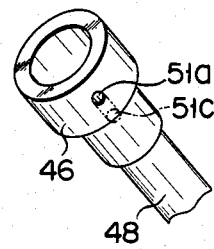

F I G. 10
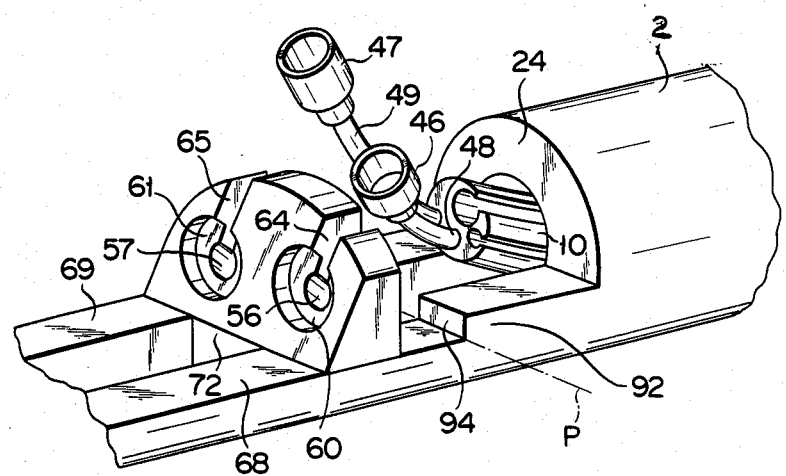
F I G. 11
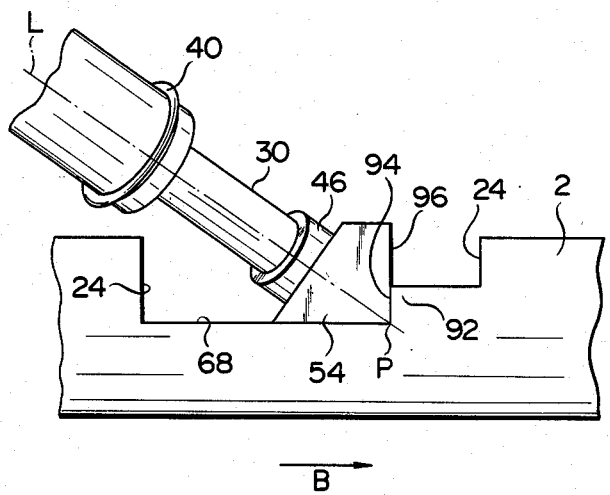

tion
ENDOSCOPE

This application is a continuation-in-part of Ser. No. 923,039, filed Oct. 24, 1986, now abandoned.

BACKGROUND OF THE INVENTION

1. Field of the Invention

The present invention relates to an endoscope with channels into which medical instruments are to be inserted, and more specifically, to an arrangement of components constituting the channels in an operating section of the endoscope, and a mounting structure for fixing the channels in the operating section.

2. Description of the Prior Art

Typical endoscopes, having channels for medical instruments, comprise channel mouthpieces attached to an operating section, and channel ducts inserted in an insertion section and connected to the channel mouthpieces. The mouthpieces and ducts constitute the whole or part of the instrument channels.

Conventional fixing means for the channel mouthpieces and ducts are stated in Japanese Patent Disclosure No. 60-210233 and Japanese Utility Model Disclosure No. 61-48701. The disclosed fixing means both include a branch cover which has an opening portion. In connecting the channel ducts and mouthpieces, the branch cover is first slid so that the ends of the ducts are drawn out through the opening portion. Thereafter, the mouthpieces are connected to the ends of the ducts.

According to this method of connection, however, the branch cover can be moved over only a very short distance, due to restrictions on the branch structure and a demand for the miniaturization of the operating section of the endoscope. Further, it is very difficult to draw out the channel ducts fully from the opening portion. Thus, the conventional working method is troublesome and time-consuming.

According to the method of connection disclosed as aforesaid, the channel ducts may possibly be pulled during connecting work. An image guide, light guide, and other elements, inserted in the insertion section of prior art endoscopes, along with the channel ducts, have a relatively low tensile strength. Therefore, these elements may sometimes be damaged during the connecting work. Also, the channel ducts can be collapsed as the branch cover is moved.

Recently, there has been an increasing demand for endoscopes of lighter weight and smaller size. Accordingly, the fixing means for fixing the channel ducts to the operating section must be miniaturized. At the same time, the mounting structure for the channel mouthpieces must be strong enough to stand external force, which may be applied if the endoscope is dropped by mistake, or when attaching or detaching a syringe or other instruments to or from the mouthpieces.

SUMMARY OF THE INVENTION

An object of the present invention is to provide an endoscope having a simple construction, in which a connecting portion for channel ducts, for medical instruments, and channel mouthpieces can be assembled with ease, and disassembly and reassembly can be easily accomplished, without damaging an image guide, light guide, or other elements therein.

Another object of the invention is to provide an endoscope, having, besides the aforesaid construction, a strong support structure, capable of satisfactorily standing external force, which may be applied to the channel ducts if the endoscope is dropped by mistake.

The above objects of the invention are achieved by an endoscope which comprises an insertion section; an operating section; an insertion member having a channel hole and disposed in the insertion section; a support tube disposed in the operating section and connected to the insertion member, the support tube having a notch; a channel duct, one end of which is connected to the channel hole of the insertion member; a mouthpiece socket connected to the other end of the channel duct; a channel mouthpiece, one end of which is removably connected to the mouthpiece socket, and the other end of which is formed with an opening; a cover member surrounding the periphery of the notch, and having an opening portion into which the channel mouthpiece is to be inserted; and a support member fixed in the notch, and having a retaining portion adapted to engage the mouthpiece socket.

Preferably, the endoscope according to the present invention comprises, besides the aforementioned arrangement, stopper means for locating the support member in a predetermined position in the notch, and supporting the support member against external force applied to the channel mouthpiece, the stopper means having a surface portion facing the channel mouthpiece.

BRIEF DESCRIPTION OF THE DRAWINGS

FIGS. 1 to 4 show an endoscope according to an embodiment of the present invention, in which FIG. 1 is a partial sectional view showing the principal part of an operating section, FIG. 2 is a front view, partially in section, showing a cover member, FIG. 3 is a side sectional view showing a joint portion between a channel mouthpiece and a channel duct, and its surroundings, and FIG. 4 is a perspective view showing mouthpiece sockets and a support member, in a state before the former are attached to the latter;

FIG. 5A is a perspective view showing a first modification of the combination of the support member and mouthpiece sockets of the endoscope, according to the first embodiment of the invention;

FIG. 5B is a perspective view showing a second modification of the mouthpiece socket;

FIG. 5C is a perspective view showing a third modification of the mouthpiece socket;

FIG. 5D is a perspective view showing a fourth modification of the mouthpiece socket;

FIGS. 10 and 11 show an endoscope according to another embodiment of the invention, in which FIG. 10 is a perspective view showing a support member and it surroundings, and FIG. 11 is a side view showing the support member and its surroundings;

DETAILED DESCRIPTION OF THE PREFERRED EMBODIMENTS

Figure 1:
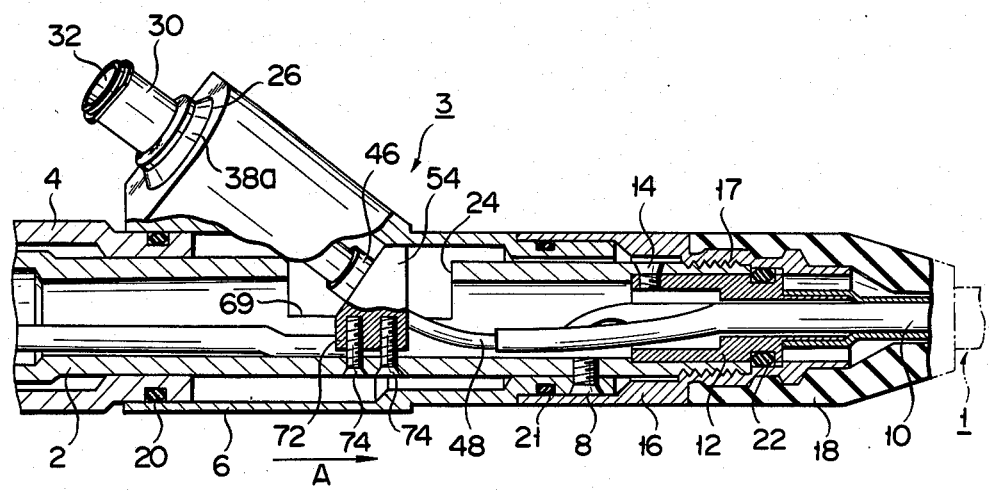
Figure 2:
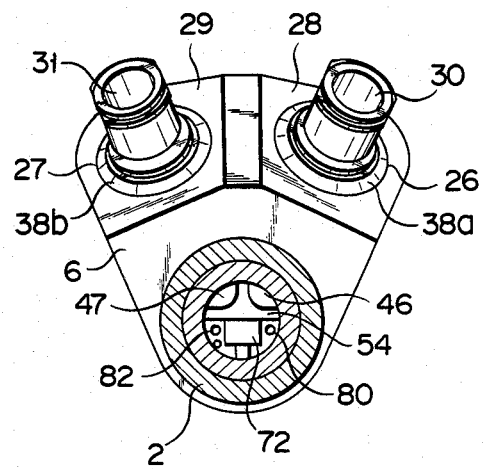

Preferred embodiments of the present invention will now be described in detail with reference to the accompanying drawings.

FIGS. 1 to 4 show an embodiment of the present invention.

In this embodiment, an endoscope comprises cylindrical support tube 2, which constitutes part of the body of an operating section 3. Cylindrical cover 4 is fitted on the outer peripheral surface of tube 2. Cover 4 is screwed to tube 2 at a predetermined portion (not shown). Cover member 6 is fitted on the outer peripheral surface of tube 2, so as to be connected to cover 4. Member 6 is slidable on the outer peripheral surface of tube 2, in the direction indicated by arrow A. After it is assembled, however, member 6 is fixed to tube 2 by means of setscrew 8. Fixing member 12 of insertion member 10 is fitted in the distal end portion of tube 2, and fixed by setscrew 14. Rubber tube 18 is slidably fitted on the outer peripheral surface of the proximal end portion of member 10. Fancy nut 16 is coupled to the proximal end portion of tube 18. It is screwed on a male-screw portion, formed on the outer peripheral surface of the distal end of support tube 2, thereby fixing rubber tube 18 to tube 2. O-rings 20, 21 and 22 are interposed between cover 4 and cover member 6, between member 6 and nut 16, and between member 12 and nut 16, respectively. Thus, the inside of the operating section 3 of the endoscope is kept watertight.

Cover member 6 is provided with a pair of opening portions 26 and 27 for channel mouthpieces, diverging sideways from member 6. When member 6 is disposed in a predetermined position, portions 26 and 27 face notch 24, which is formed in the side wall of support tube 2. A shown in FIG. 2 and 3, moreover, opening portions 26 and 27 are formed at two branch portions 28 and 29 of cover member 6, respectively. Channel mouthpieces 30 and 31 are inserted in portions 26 and 27, respectively.

Figure 3:
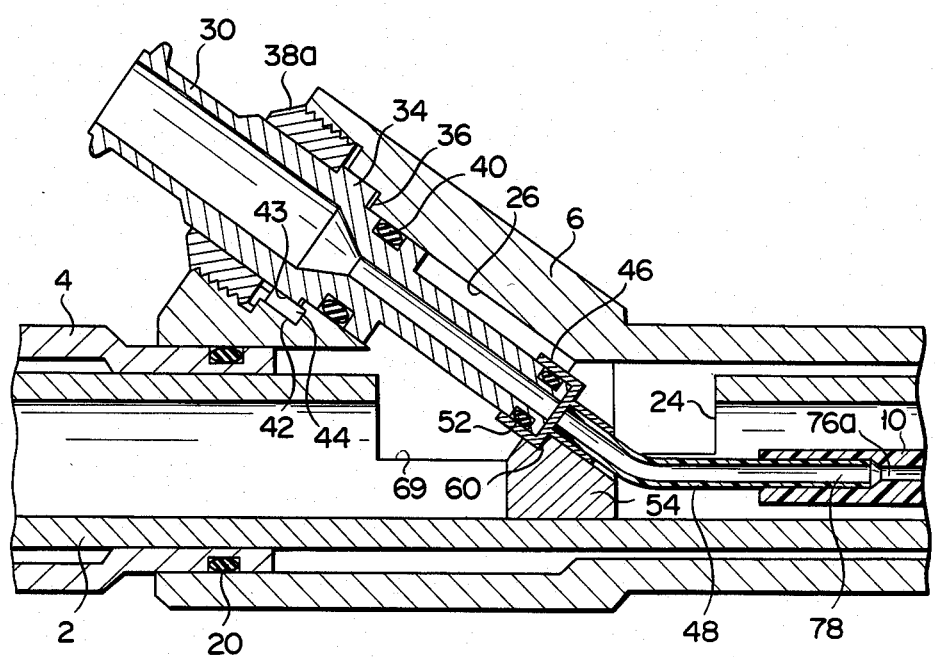

Channel mouthpiece 30 will now be described in detail. Flange portion 34, which is formed at the middle portion of mouthpiece 30, engages shoulder portion 36 inside opening portion 26, for temporary retention. After mouthpiece 30 is connected to insertion member 10 by means of another member, flange portion 34 is located in a position at a short distance from shoulder portion 36, and fixing ring 38a is fitted on mouthpiece 30, as shown in FIG. 3. Ring 38a is screwed in a female-screw portion on the inner surface of opening portion 26, and pushes in flange portion 34 of channel mouthpiece 30, thereby holding the mouthpiece in position. O-ring 40 is fitted in a groove, formed on the outer peripheral surface of mouthpiece 30, thereby maintaining the water-tightness of the inside of the endoscope. Opening portion 26 and flange portion 34 are formed with grooves 42 and 43, respectively. Pin 44 is fitted in both grooves 42 and 43, whereby mouthpiece 30 is prevented from rotating.

Channel mouthpiece 31 has the same construction and function as mouthpiece 30, so its description is omitted herein.

As shown in FIG. 3, the distal end portions of channel mouthpieces 30 and 31 are connected to mouthpiece sockets 46 and 47, respectively. Sockets 46 and 47 are connected to the respective proximal end portions of channel ducts 48 and 49, each formed of a flexible tube or a metal pipe. O-ring 52 is fitted on the distal end portion of each channel mouthpiece. Thus, the junction between the mouthpiece and its corresponding mouthpiece socket is sealed.

Figure 4:
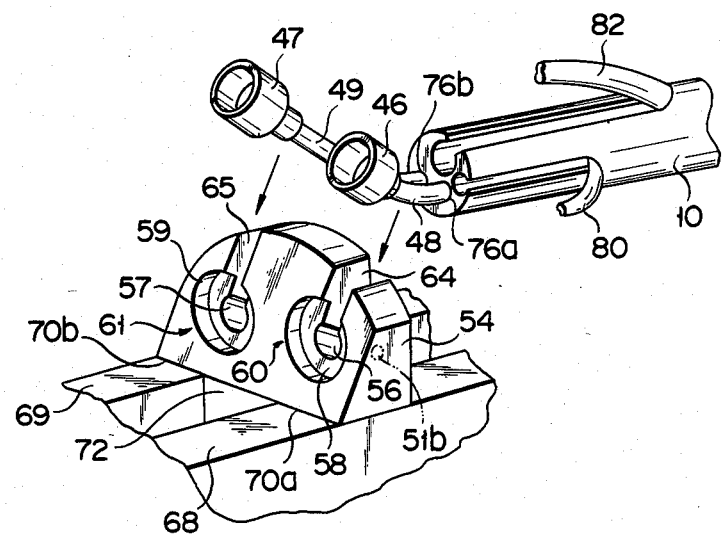

As shown in FIG. 4, support member 54 for supporting mouthpiece sockets 46 and 47 has a pair of retaining portions 60 and 61, which are formed of holes 56 and 57 and recesses 58 and 59, respectively. Channel ducts 48 and 49 are passed through holes 56 and 57, respectively, and sockets 46 and 47 are fitted in recesses 58 and 59, respectively. Slits 64 and 65, continuous with holes 56 and 57, respectively, are formed in the top portion of support member 54. Thus, ducts 48 and 49 can be fitted into their corresponding holes 56 and 57 via slits 64 and 65, respectively.

Support member 54 has a protrusion 72 at the bottom. Protrusion 72 is inserted into support pipe 2 through notch 24 thereof. Member 54 is located in position as shoulder portions 70a and 70b, formed on either side of protrusion 72, abut against top faces 68 and 69 of notch 24, respectively. Then, member 54 is fixed to support tube 2 by means of screws 74, as shown in FIG. 1.

As shown in FIG. 4, channel ducts 48 and 49 are connected to channel holes 76a and 76b, respectively, of insertion member 10. Each channel duct and its corresponding channel hole constitute integral channel 78.

Besides channel ducts 48 and 49, image guide 80 and light guide 82 are passed through insertion member 10, as shown in FIG. 4. Guides 80 and 82 are led out sideways from the side wall of the proximal end portion of insertion member 10, skirt around protrusion 72 of support member 54, and extend through support tube 2 to the operating section.

A procedure of assembling the branch portions will now be described.

First, channel ducts 48 and 49 are inserted into and bonded to channel holes 76a and 76b, respectively, of insertion member 10. Mouthpiece sockets 46 and 47 are attached to the other ends of ducts 48 and 49, respectively. Then, fixing member 12, fancy nut 16, and rubber tube 18 are fitted on insertion member 10. In doing this, nut 16 is left slidable with tube 18, without being screwed on the male-screw portion 17 of support tube 2.

At the operating section, on the other hand, cover 4 and cover member 6 are fitted on the outer peripheral surface of support tube 2. Member 6 is slid in the direction of arrow A of FIG. 1, to a position where setscrew 14 is exposed. The cover member 6 is located temporarily in this position. Then, channel ducts 48 and 49, with mouthpiece sockets 46 and 47 attached thereto, fixing member 12, and insertion member 10 are inserted into support tube 2, and sockets 46 and 47 are taken out through notch 24 of tube 2. At the same time, member 12 is fixed in tube 2 by means of setscrew 14. Subsequently, ducts 48 and 49 are fitted into their corresponding slits 64 and 65 of support member 54, and sockets 46 and 47 are held in position in recesses 58 and 59 of retaining portions 60 and 61, respectively, as shown in FIG. 4.

Thereafter, support member 54 is fixed to support tube 2 by means of screws 74, as shown in FIG. 1. In doing this, member 54 is fixed in position so that shoulder portions 70a and 70b abut against top faces 68 and 69, respectively, of notch 24.

Then, cover member 6 is slid in the direction opposite to the direction of arrow A of FIG. 1, so as to be located in a predetermined position where it covers the whole periphery of notch 24. In this position, member 6 is fixed to support tube 2 by means of setscrew 8.

Thereafter, fancy nut 16 and rubber tube 18, having so far been located temporarily around insertion member 10, are slid in the direction opposite to arrow A, and nut 16 is screwed on the male-screw portion 17 of support tube 2. Thus, nut 16 and tube 18 are fixed to tube 2.

Then, pins 44 are fitted individually into grooves 42 at opening portions 26 and 27 of cover member 6, and channel mouthpieces 30 and 31 are inserted into their corresponding opening portions so that grooves 43 on their respective outer peripheral surfaces are in alignment with pins 44. At the same time, the distal end portions of mouthpieces 30 and 31, each fitted previously with O-rings 40 and 52, are inserted into mouthpiece sockets 46 and 47, respectively.

Finally, fixing rings 38a and 38b are screwed into the respective female-screw portions of the opening portions 26 and 27 of cover member 6. Thus, flange portions 34 are pushed into their corresponding opening portions, and fixed, by rings 38a and 38b.

FIG. 5A shows a modification of a combination of the support member and mouthpiece sockets of the endoscope, according to the first embodiment of the present invention. In this modification, recesses 58 and 59 at retaining portions 60 and 61 of support member 54 are not perfectly circular, having partial flat portions 83a and 83b, respectively. Corresponding to portions 83a and 83b, flat faces 84a and 84b are formed partially on the respective outer peripheral surfaces of mouthpiece sockets 46 and 47.

Thus, when mouthpiece sockets 46 and 47 are fitted into retaining portions 60 and 61, respectively, flat portions 83a and 83b engage their corresponding flat faces 84a and 84b, thereby preventing channel ducts 48 and 49 and sockets 46 and 47 from rotating. If medical instruments are inserted into channels 78, therefore, ducts 48 and 49 cannot rotate and damage image guide 80 or light guide 82, passed through insertion member 10, along with the ducts.

According to a second modification, as shown in FIG. 5B, mouthpiece sockets 46 and 47 and their corresponding recesses 58 and 59 may, for example, be polygonal in shape. According to a third modification, as shown in FIG. 5C, the outer peripheral surfaces of sockets 46 and 47 and the inner peripheral surfaces of recesses 58 and 59 may be tapered so that the sockets are prevented from rotating as tapered surfaces 50 engage one another. FIG. 5D shows a fourth modification, in which blind hole 51a is formed in the outer peripheral surface of each of mouthpiece sockets 46 and 47, and recesses 58 and 59 of support member 54 are each formed with a through hole 51b, extending from the inner peripheral surface of each recess to the outside. When the sockets are fitted in their corresponding recesses, each blind hole 51a and its corresponding through hole 51b are arranged in a straight line. Thereafter, a pin 51c is inserted into the holes to fix the sockets in position.

Figure 6:
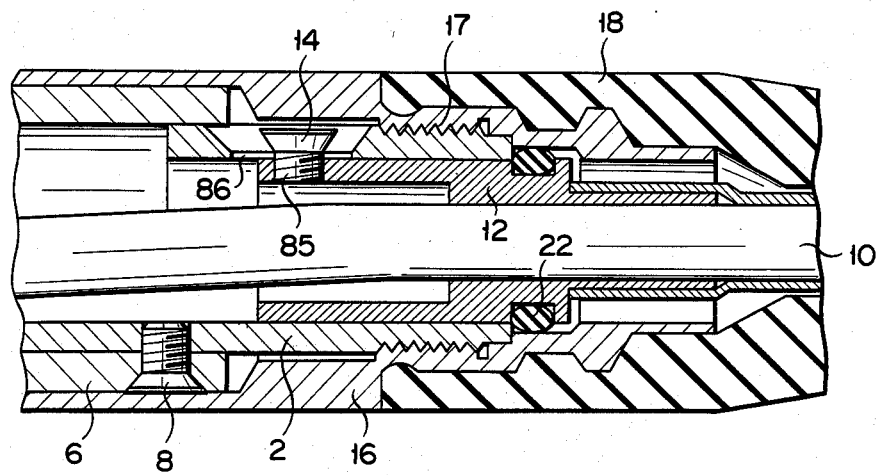
FIG. 6 is a side sectional view showing a modification of fixing means for fixing the mouthpiece to a support tube.
Figure 7:
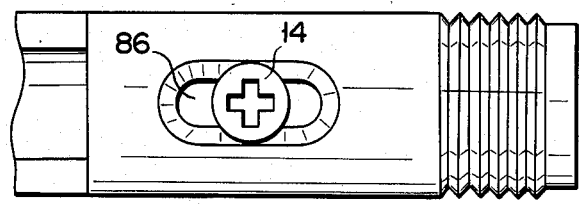
FIG. 7 is a plan view of the distal end portion of the support tube, with the fixing means thereon.

FIGS. 6 and 7 show a modification of fixing means for fixing mouthpiece 12 to support tube 2, used in the endoscope according to the present invention.

The fixing means includes female-screw portion 85 formed in fixing member 12, insertion hole (non-tapped hole) 86 formed in support tube 2, and setscrew 14 for fixing member 12 to tube 2. Portion 85 is in the form of a slot elongated in the axial direction of insertion member 10. Thus, member 12 can move in the axial direction, to be fixed in any desired position.

According to the fixing means of this modification, even though those portions of insertion member 10 and channel ducts 48 and 49, between fixing member 12 and mouthpiece sockets 46 and 47, are subject to variations in length, channel mouthpieces 30 and 31 can be located in fixed positions relative to support member 54, by sliding member 12.

Figure 8:
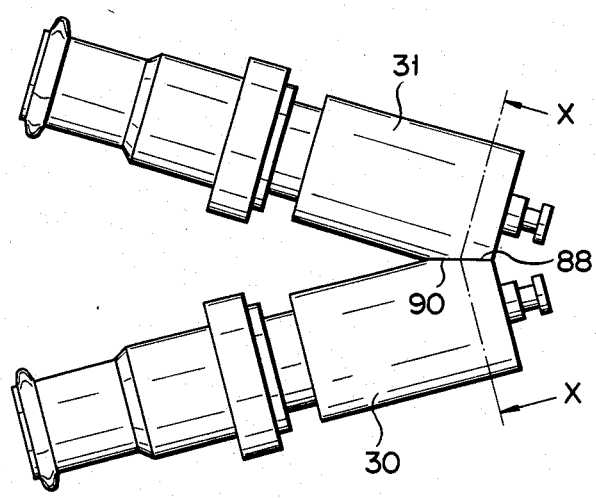
FIG. 8 is a plan view showing a modification of a channel mouthpiece.
Figure 9:
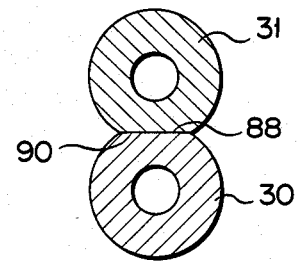
FIG. 9 is a sectional view taken along line X—X of FIG. 8.

FIGS. 8 and 9 show a modification of the channel mouthpieces of the endoscope according to the present invention. In this modification, the peripheral surfaces of the respective distal end portions of channel mouthpieces 30 and 31, fitted in opening portions 26 and 27 of cover member 6, are partially cut off at a slant on the axes of mouthpiece 30 and 31, thus forming slant portions 88 and 90. If portions 88 and 90 are opposed to each other when mouthpieces 30 and 31 are inserted into opening portions 26 and 27, respectively, the portions 88 and 90 are joined and fixed together.

As a result, channel mouthpieces 30 and 31 are prevented from rotating. Thus, the arrangement of this modification is simpler than the means for preventing the rotation of the channel mouthpieces, using the pins, according to the aforementioned embodiment.

FIGS. 10 and 11 show an endoscope according to another embodiment of the present invention. In this embodiment, as shown in FIG. 10, step portions 92, serving as stoppers for support member 54, are formed individually on top faces 68 and 69 of notch 24 of support tube 2, adjoining insertion member 10. When member 54 is moved in the direction of arrow B, as shown in FIG. 11, side wall 96 of member 54 abuts against and comes into close contact with end faces 94, which define step portions 92, individually. Thus, member 54 is prevented from moving further. Also, as shown in FIG. 11, straight line P connecting the boundary lines between top faces 68 and 69 of notch 24 and end faces 94 of step portions 92 passes through the point of intersection of respective axes L of channel mouthpieces 30 and 31. Other portions of this second embodiment are constructed in the same manner as in the first embodiment.

In assembling the endoscope according to the second embodiment, support member 54 is moved in the direction of arrow B after protrusion 72 is fitted into support tube 2 through notch 24. During this process, side wall 96 of member 54 abuts against end faces 94 of step portions 92, so that member 54 is located in position. Thereafter, support member 54 is fixed to support tube 2 by means of screws 74, as shown in FIG. 1. Other components of the second embodiment are assembled in the same manner as in the first embodiment.

The mounting structure for the support member of the second embodiment is designed as described above. Thus, support member 54 is located as it is in contact with top faces 68 and 69 of notch 24 and end faces 94 of step portions 92, as shown in FIG. 10. As a result, the location of the support member is easy, and its mounting accuracy is improved. Since member 54 is supported by faces 68, 69 and 94, as well as by screws 74, it is fixed securely to support tube 2. Moreover, straight line P, connecting the boundary lines between top faces 68 and 69 and their corresponding end faces 94, passes through the point of intersection of axes L of channel mouthpieces 30 and 31. Therefore, if any external force, transmitted through mouthpieces 30 and 31, is applied to support member 54, it scatters in two directions, along top faces 68 and 69 and end faces 94. Attached to the corner portion defined by faces 68, 69 and 94, moreover, support member 54 is prevented from rotating in the axial direction of support tube 2. Accordingly, screws 74 for fixing member 54 cannot be subjected to any excessive force.

According to the first and second embodiments, flange portions 34 of channel mouthpieces 30 and 31 never engage shoulder portions 36 of opening portions 26 and 27. Therefore, the distal ends of mouthpieces 30 and 31 are brought into close contact with mouthpiece sockets 46 and 47, respectively, so that they cannot slip off. Although this arrangement imposes an extra load on support member 54, it also helps member 54 withstand the load satisfactorily.

Figure 12:
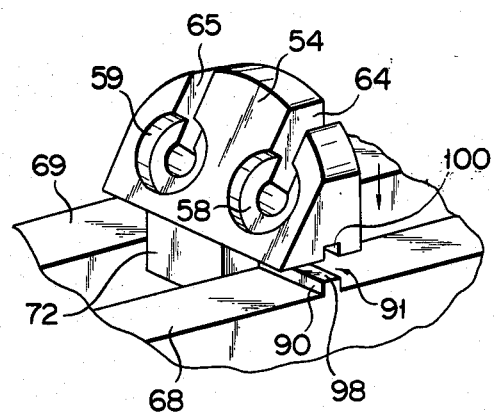
FIG. 12 is a perspective view showing a modification of a step portion according to the second embodiment.
Figure 13:
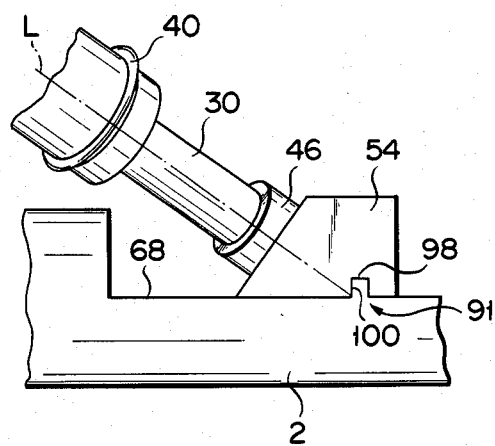
FIG. 13 is a side view showing the step portion of FIG. 12 and its surroundings.

FIGS. 12 and 13 show a modification of the step portion according to the second embodiment. In this modification, ridges 98 for fixing support member 54 are formed individually on top faces 68 and 69 of notch 24. They are integral with support tube 2. On the other hand, recesses 100 are formed in the undersurface of member 54, corresponding to ridges 98. Thus, when recesses 100 of member 54 closely engage ridges 98 of notch 24 of tube 2, member 54 is held in position inside notch 24, and fixed by screws 74.

As shown in FIG. 13, axes L of channel mouthpieces 30 and 31 are substantially in line with the roots of their corresponding ridges 98. Accordingly, the ridges, like the step portions of the second embodiment, can support the support member firmly.

Figure 14:
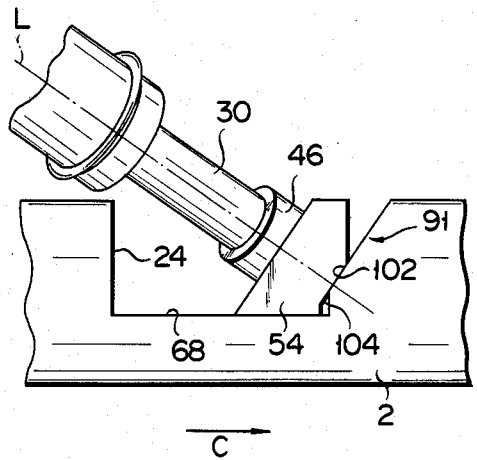
FIG. 14 is a side view showing another modification of the step portion.

FIG. 14 shows a second modification of the step portion of the second embodiment. In this modification, slant surface 102, intersecting axes L of channel mouthpieces 30 and 31 at right angles, is formed on the wall of notch 24 of support tube 2. On the other hand, slant portion 104 is formed on part of support member 54, corresponding to surface 102. When member 54 is moved in the direction of arrow C, portion 104 abuts against and comes into close contact with surface 102 of notch 24. Thus, support member 54 is located in a fixed position, relative to notch 24 of support tube 2, and then fixed in the same position by means of screws 74.

Slant surface 102 of notch 24 and slant portion 104 of support member 54 engage each other on the extensions of axes L of channel mouthpieces 30 and 31. Therefore, external force applied to mouthpieces 30 and 31 is received by surface 102 of notch 24, and it cannot be transmitted to screws 74.

The slant surface of this modification, like the step portions of the second embodiment, can support the support member firmly.

In all of the embodiments and modifications described above, channel mouthpieces are two in number. Alternatively, however, only one, or three or more channel mouthpieces may be used with the same result.

In the endoscope according to the present invention, as described in detail herein, the channel mouthpieces and channel ducts can be assembled easily and quickly. Moreover, the endoscope of the invention can enjoy compactness and durability, without any distortion of its joint portion by external force on the channel mouthpieces.

Figure 15:
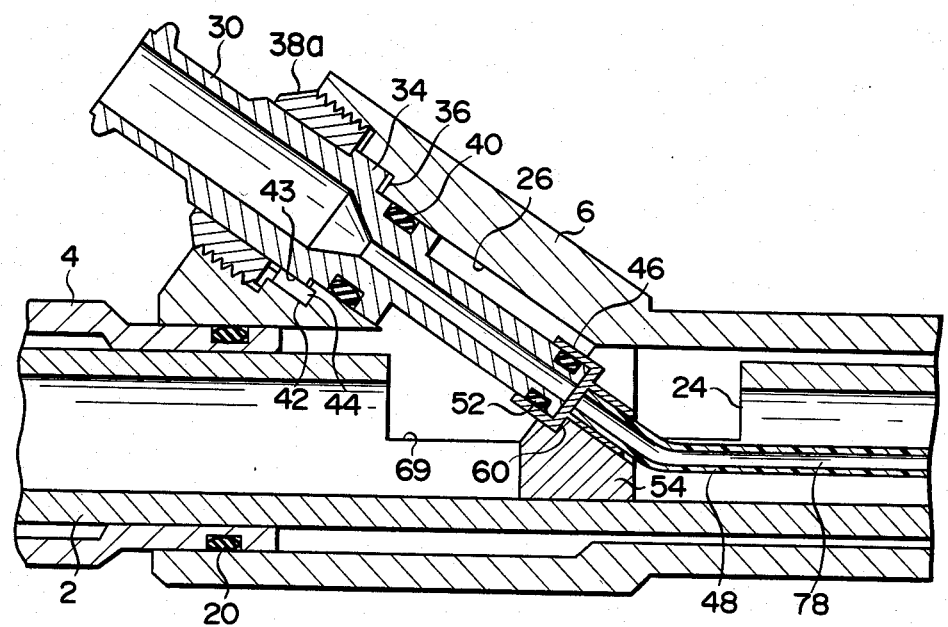
FIGS. 15 and 16 show another embodiment of the endoscope of the present invention.
Figure 16:
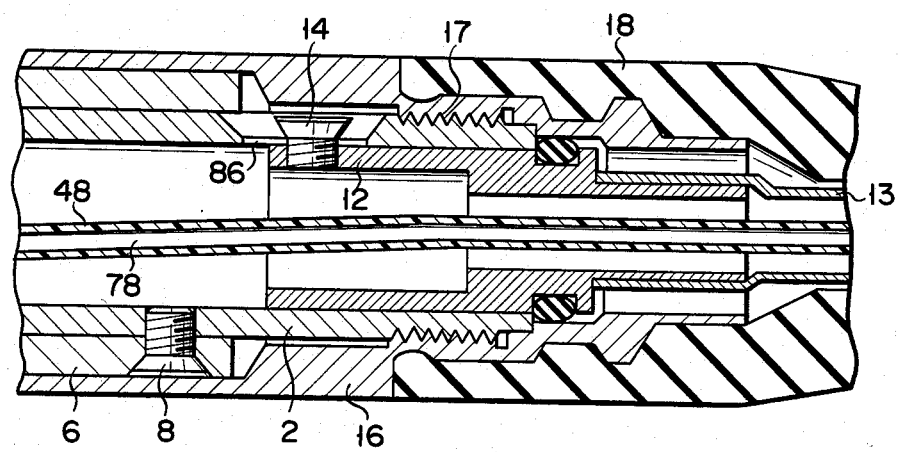

The path between the distal end of channel mouthpiece and the distal end of insertion section 1 need not be defined in the manner mentioned above. It can be alternatively defined in the manner illustrated in FIGS. 15 and 16. This alternative embodiment will be described.

In the above-mentioned embodiment, insertion member 10 having channel hole 76a is located in the interior of insertion section 1, and the distal end of channel duct 48 is connected to the opening at the proximal end of channel hole 76a. Mouthpiece socket 46 is connected to the proximal end of channel duct 48 such that channel duct 48 and insertion member 10 define a path extending between the internal hole of channel socket 30 and the distal end of insertion section 1. In the alternative embodiment, in contrast, channel duct 48 is extended from mouthpiece socket 46 to the distal end of insertion section 1, thereby eliminating the use of insertion member 10. With this construction, the number of parts required can be reduced. In addition, the step of connecting channel duct 48 and insertion member 10 together can be omitted from the manufacturing process of the endoscope.

Inner sheath 13 is located within insertion section 1. Channel duct 48 and insertion member 10 are received in inner sheath 13 for protection. Further, bundles of optical fibers, such as an image guide and a light guide (neither is shown), are also received in inner sheath 13 for protection.

What is claimed is:

1. An endoscope, comprising:
   an insertion section;
   an operation section;
   a channel duct disposed in the insertion section, the channel duct having a distal end and a proximal end;
   a support tube located in the operation section and having a notch;
   a mouthpiece socket connected to the proximal end of the channel duct;
   a channel mouthpiece, one end of which is detachably connected to the mouthpiece socket and another end of which is formed with an opening;
   a cover member surrounding the periphery of the notch and having an opening through which the channel mouthpiece is inserted; and
   a support member fixed in the notch and having retaining means adapted to engage the mouthpiece socket.

2. An endoscope according to claim 1, further comprising:
   an insertion member located within the insertion section and connected to the distal end of the channel duct, the insertion member having a channel hole.

3. An endoscope according to claim 1, wherein the support member has a plurality of retaining means, the cover member has holes which are the same in number as the retaining means of the support member, and the endoscope further comprises channel ducts, mouthpiece sockets, and channel mouthpieces which are the same in number as the retaining means of the support member.

4. An endoscope according to claim 1, wherein the retaining means of the support member includes a recess to receive the mouthpiece sockets, a hole portion formed in the center of the recess, and a slit continuous with the hole portion, and the channel duct can be fitted into the hole portion through the slit.

5. An endoscope according to claim 4, wherein the mouthpiece socket is cylindrical, and the recess of the support member is ring-shaped.

6. An endoscope according to claim 4, wherein the mouthpiece socket is in the form of a cylinder partially having a flat portion, and the recess of the support member is in the form of a ring partially having a flat portion, corresponding to the flat portion of the socket, the two flat portions being adapted to engage each other, thereby preventing the socket from rotating.

7. An endoscope according to claim 4, wherein the mouthpiece socket has a polygonal cross section, and said recess of the support member has a cross section corresponding in shape to that of the socket, said recess being adapted to engage the socket, thereby preventing the socket from rotating.

8. An endoscope according to claim 4, wherein the outer peripheral surface of the mouthpiece socket and the inner peripheral surface of the recess of the support member are tapered, the tapered surfaces being adapted to come into frictional contact with each other, thereby preventing the socket from rotating.

9. An endoscope according to claim 4, wherein the outer peripheral surface of the mouthpiece socket is formed with a blind hole, the recess of the support member is formed with a through hole extending from the inner peripheral surface of the recess to the outside, and a pin is inserted into the blind hole through the through hole, thereby preventing the socket from rotating.

10. An endoscope according to claim 1, further comprising: an adjust means, located at the distal end of the support tube, for adjusting the relative position between the mouthpiece socket and the retaining means.

11. An endoscope according to claim 10, wherein the adjust means includes:
an adjust member inserted in an opening at the distal end of the support tube and slidable in the axial direction thereof;
an elongated hole formed in the vicinity of the distal end of the support tube and elongated in the axial direction; and
a fixing screw inserted through the elongated hole and threadedly fitted in the side wall of the support member, the adjust member being fixed or released from the support tube by use of the fixing screw.

12. An endoscope according to claim 1, further comprising:
a male-screw portion formed on the outer peripheral surface of the distal end portion of the support tube, a fancy nut screwed on the male-screw portion, and a rubber tube fitted on the outer peripheral surface of the fancy nut and serving to maintain the watertightness of the inside of the support tube.

13. An endoscope according to claim 3, wherein each the channel mouthpiece has a slant surface on part of the outer peripheral surface of the distal end portion thereof, so that the respective slant surfaces of the mouthpieces are brought closely into contact with each other, thereby preventing the mouthpieces from rotating, when the mouthpieces are inserted into the opening portions of the cover member.

14. An endoscope according to claim 1, wherein the channel duct is formed of a metal pipe.

15. An endoscope according to claim 1, wherein the channel duct is formed of a flexible tube.

16. An endoscope according to claim 1, further comprising: a stopper means for enabling the support member to be located at a predetermined position within the notch, the stopper means having a surface portion facing the channel mouthpiece and holding the support member against external force to be applied to the channel mouthpiece.

17. An endoscope according to claim 16, wherein the surface portion of the stopper means intersects with the extensions of the axes of the channel mouthpiece.

18. An endoscope according to claim 16, wherein the stopper means includes a pair of step portions formed at the corner portions of the notch.

19. An endoscope according to claim 16, wherein the stopper means includes a pair of projections formed on the bottom portions of the notch and having the surface portion, and a recess formed on the undersurface of the support member and adapted to engage the projections.

20. An endoscope according to claim 17, wherein the stopper means includes a pair of slant surfaces formed on the side walls of the notch and having the surface portion, and a slant portion formed on the lower portion of the side wall of the support member and adapted to come into close contact with the slant surfaces, the slant surfaces being perpendicular to the extension.

* * * * *